US00PP12598P2

(12) United States Plant Patent
Koppe

(10) Patent No.: US PP12,598 P2
(45) Date of Patent: Apr. 30, 2002

(54) BEGONIA PLANT NAMED 'BETULIA PINK'

(75) Inventor: Lubbertus H. Koppe, Ermelo (NL)

(73) Assignee: Koppe Veredelins, B.V., Ermelo (NL)

( * ) Notice: Subject to any disclaimer, the term of this patent is extended or adjusted under 35 U.S.C. 154(b) by 0 days.

(21) Appl. No.: 09/641,718

(22) Filed: Aug. 21, 2000

(51) Int. Cl.[7] ..... A01H 5/00
(52) U.S. Cl. ..... Plt./348
(58) Field of Search ..... Plt./348

(56) References Cited

PUBLICATIONS

UPOV–ROM GTITM Computer Database 2001/03, G?TI Jouve Retrieval Software, citation for 'Betulia Pink'.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Begonia plant named 'Betulia Pink', characterized by its compact and freely branching plant habit; double dark pink flowers; short peduncles and short pedicels; and excellent postproduction longevity.

2 Drawing Sheets

BACKGROUND OF THE INVENTION

The present Invention relates to a new and distinct cultivar of Begonia plant, botanically known as *Begonia×hiemalis*, commercially known as Elatior Begonia, and hereinafter referred to by the name 'Betulia Pink'.

The new Begonia was discovered by the Inventor in a controlled environment in Ermelo, The Netherlands, in April, 1997, as a naturally-occurring whole plant mutation of *Begonia×hiemalis* 'Betulia', disclosed in U.S. Plant Pat. No. 10,475. The new Begonia was observed as a single plant in a group of flowering plants of the parent cultivar. The selection of this plant was based on its unique flower color and plant size.

Asexual reproduction of the new Begonia by leaf and terminal cuttings taken in a controlled environment in Ermelo, The Netherlands, has shown that the unique features of this new Begonia are stable and reproduced true to type in successive generations.

SUMMARY OF THE INVENTION

The cultivar 'Betulia Pink' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Betulia Pink'. These characteristics in combination distinguish 'Betulia Pink' as a new and distinct Begonia:

1. Compact and freely branching plant habit.
2. Double dark pink-colored flowers.
3. Short peduncles and short pedicels.
4. Excellent postproduction longevity.

In side-by-side comparisons conducted by the Inventor in Ermelo, The Netherlands, plants of the new Begonia differ from plants of the parent cultivar Betulia primarily in flower color as plants of 'Betulia' have red-colored flowers:

BRIEF DESCRIPTION OF THE PHOTOGRAPHS

The accompanying colored photographs illustrate the overall appearance of the new Begonia, showing the colors as true as it is reasonably possible to obtain in colored reproductions of this type. Colors in the photographs may differ slightly from the color values cited in the detailed botanical description which more accurately describe the actual colors of the new Begonia.

The photograph on the first sheet comprises a side perspective view of a typical flowering plant of 'Betulia Pink'.

The photographs on the second sheet, from top to bottom, are close-ups of the upper surfaces of typical developing flowers, the lower surfaces of typical developing flowers, the upper surfaces of typical developing leaves, and the lower surfaces of typical developing leaves.

DETAILED BOTANICAL DESCRIPTION

In the following description, color references are made to The Royal Horticultural Society Colour Chart except where general terms of ordinary dictionary significance are used. The following observations and measurements describe plants grown in Ermelo, The Netherlands, under commercial practice in a glass-covered greenhouse. Average day and night temperatures were 20° C. during the first three to four weeks then lowered to an average day and night temperature of 19° C. until flowering. Four weeks after planting in 12-cm containers, one week of long nyctoperiods were given followed by short nyctoperiods of eight hours. Measurements and numerical values represent averages for typical flowering plants.

Botanical classification: *Begonia×hiemalis* cultivar Betulia Pink.

Commercial classification: Elatior Begonia.

Parentage: Naturally-occurring whole plant mutation of *Begonia×hiemalis* cultivar Betulia, disclosed in U.S. Plant Pat. No. 10,475.

Propagation:

*Type.*—Terminal cuttings.

*Time to develop roots.*—About 42 days with soil temperatures of 20° C.

*Root description.*—Fine, fibrous and well-branched; plants typically do not form tubers.

Plant description:

*Plant form.*—Compact; upright and rounded potted plant; freely branching with good stem and stem base strength. Flowers are double and abundant. Plants flower continuously.

*Growth habit.*—Moderate growth rate, vigorous. Suitable for 11 to 15-cm containers. Under optimal environmental and cultural conditions, usually about 4 months are required to produce proportional 13-cm potted plants from terminal cuttings. Vegetative shoots are formed at basal nodes and flowering shoots are formed at upper nodes.

*Plant height.*—*About* 17.5 cm.

*Plant width.*—About 23 cm.

*Leaves.*—Arrangement: Simple, alternate. Length: About 10.5 cm. Width: About 8.5 cm. Shape: Asymmetrical, more or less reniform. Apex: Acuminate. Base: Cordate. Margin: Doubly serrate. Texture: Glabrous. Petiole length: About 5 cm. Color, young and fully expanded leaves: Upper surface: 147A. Lower surface: 191B to 191C. Venation: 144A. Petiole: 60A.

Flower description:

*Flowering habit.*—Double flowers with numerous tepals arranged in axillary cymes. Usually 6 to 10 flowers per cyme. Many cymes in flower simultaneously. Flowering continuous.

*Natural flowering season.*—Plants will flower year around regardless of nyctoperiod, however plants flower earlier and more abundantly from mid-February until November in the Northern hemisphere.

*Flowers.*—Shape: Rounded. Diameter: about 5 cm. Depth (height): About 2 cm.

*Flower buds.*—Length: About 1.75 cm. Diameter: About 1.25 cm. Color: 53B.

*Tepals.*—Arrangement: Rosette. Shape: Rounded flabellate; apex, rounded. Margin: Entire. Quantity per flower: Usually about 16 per flower. Size: Outer tepals: Length: About 2.75 cm. Width: About 2.75 cm. Inner tepals: Length: About 2 cm. Width: About 1.7 cm. Texture: Smooth, satiny, glabrous. Color: When opening: 57A. Fully opened, upper surface: 57A. Fully opened, lower surface: 58B.

*Flower bracts.*—Arrangement: Two, opposite. Shape: Broadly cordate; apex, apiculate. Margin: Serrate. Color, both surfaces: 139D with anthocyanin.

*Peduncles.*—Angle: Erect. Length: About 4 cm. Texture: Slightly pubescent. Color: 173B.

*Pedicels.*—Angle: Erect. Length: About 1.4 cm. Texture: Pubescent. Color: 180A.

*Reproductive organs.*—Stamens: None observed. Pistils: None observed.

*Seed.*—Seed production has not been observed as reproductive organs are not formed.

Postproduction longevity:

*Individual flowers.*—Generally about 2 to 3 weeks.

*Whole plants.*—About 6 weeks under interior conditions.

Disease resistance: Resistance to diseases common to Begonia has not been determined.

It is claimed:

1. A new and distinct cultivar of Begonia plant named 'Betulia Pink', as illustrated and described.

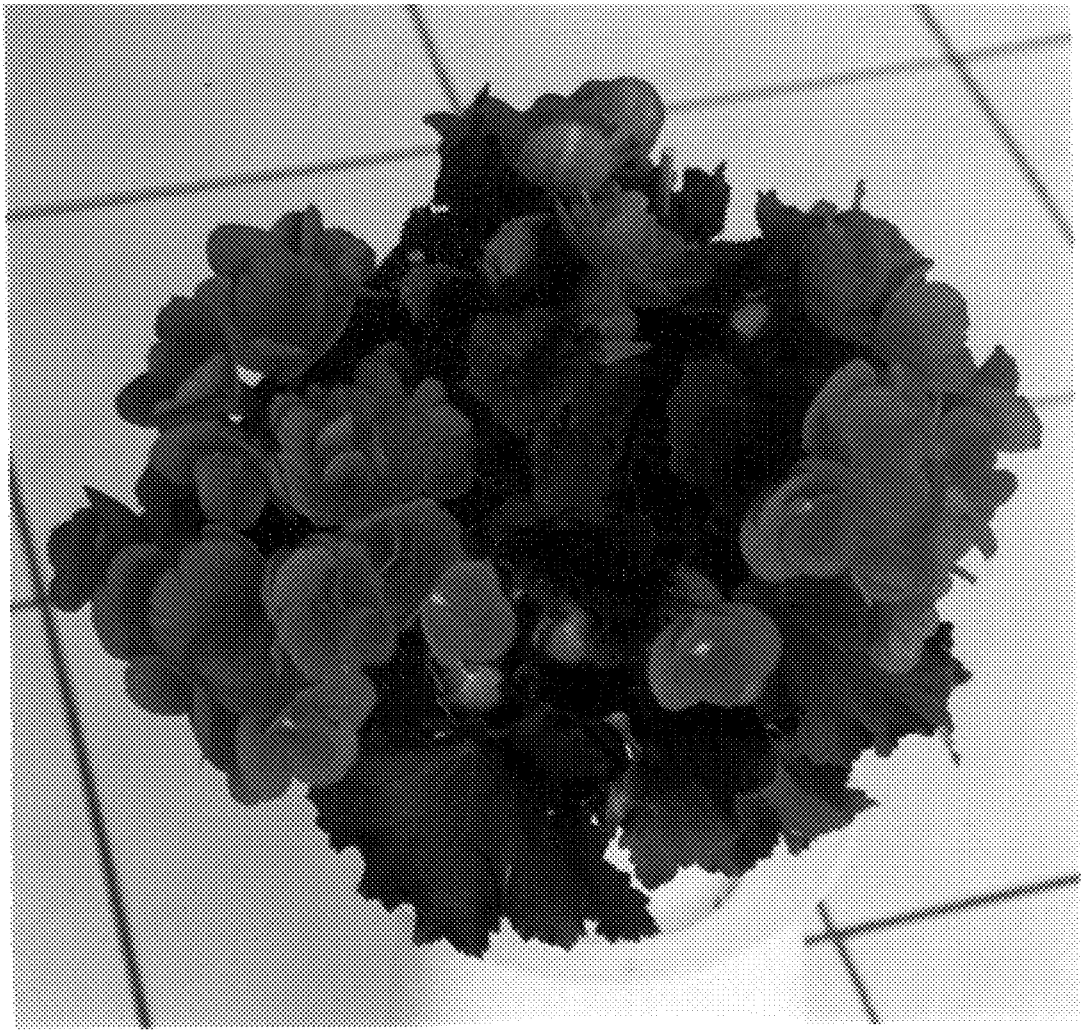

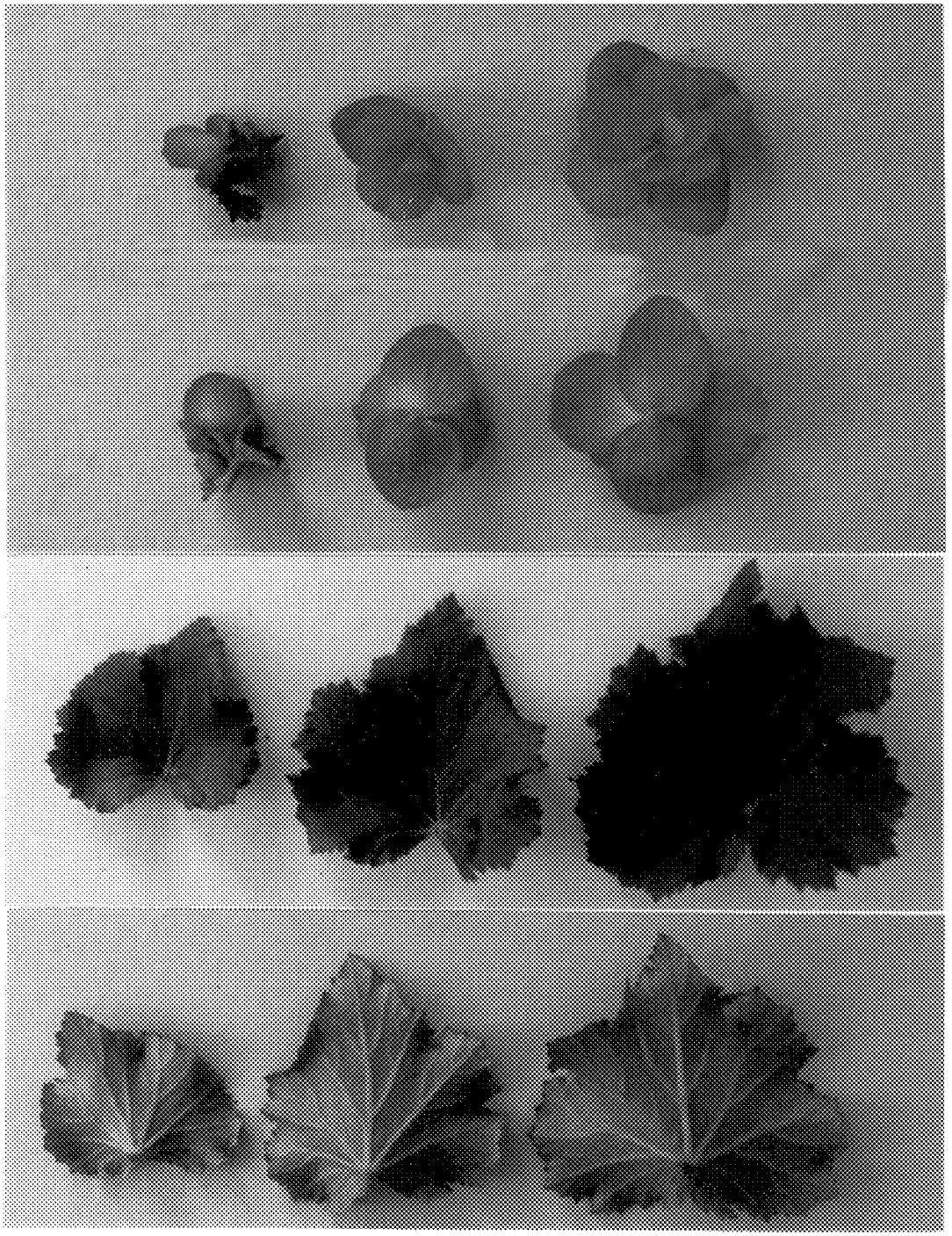

* * * * *